(12) United States Patent
Medoff et al.

(10) Patent No.: US 8,900,841 B2
(45) Date of Patent: Dec. 2, 2014

(54) PROCESSING BIOMASS

(71) Applicant: Xyleco, Inc., Woburn, MA (US)

(72) Inventors: Marshall Medoff, Brookline, MA (US); Thomas Craig Masterman, Brookline, MA (US); Michael W. Finn, Somerville, MA (US)

(73) Assignee: Xyleco, Inc., Woburn, MA (US)

( * ) Notice: Subject to any disclaimer, the term of this patent is extended or adjusted under 35 U.S.C. 154(b) by 0 days.

(21) Appl. No.: 14/016,484

(22) Filed: Sep. 3, 2013

(65) Prior Publication Data

US 2014/0038251 A1 Feb. 6, 2014

Related U.S. Application Data

(63) Continuation of application No. PCT/US2012/071097, filed on Dec. 20, 2012.

(60) Provisional application No. 61/579,552, filed on Dec. 22, 2011, provisional application No. 61/579,559, filed on Dec. 22, 2011.

(51) Int. Cl.
*C12P 1/04* (2006.01)
*C12P 19/24* (2006.01)
*C12P 19/14* (2006.01)
*C12P 7/16* (2006.01)

(52) U.S. Cl.
CPC ............... *C12P 19/24* (2013.01); *C12P 19/14* (2013.01); *C12P 7/16* (2013.01); *Y02E 50/10* (2013.01)
USPC ..................................................... 435/170

(58) Field of Classification Search
None
See application file for complete search history.

(56) References Cited

U.S. PATENT DOCUMENTS

| | | | |
|---|---|---|---|
| 2010/0285552 A1* | 11/2010 | Varanasi et al. | 435/161 |
| 2011/0279371 A1* | 11/2011 | Ma | 345/163 |
| 2011/0296747 A1* | 12/2011 | Sonomoto et al. | 44/451 |

FOREIGN PATENT DOCUMENTS

JP 2001000200 1/2001

OTHER PUBLICATIONS

Tashiro et al., Journal of Bioscience and Bioengineering, vol. 98, Issue 4, 2004, pp. 263-268.*
ATCC Product Sheet, retrieved from the Internet: www.atcc.org.*
Lima et al., "Fructose Syrup: A Biotechnology Asset", Food Technology and Biotechnology, vol. 49, Oct. 2011, pp. 424-434.
Database WPI 2001 Thomson Scientific, London, GB, "Production of High Fructose Isomer, Involves Fractionating Part of Glucose Rich Fraction to Obtain Oligosaccharide Rich and Deficient Fractions, and Circulating Oligosaccharide Deficient Fraction for Isomerization".
Shi et al., "Large Number of Phosphotransferase Genes in the *Clostridium beijerinckii* NCIMB 8052 Genome and the Study on their Evolution", BMC Bioinformatics, vol. 11, (Suppl 11), 2010, pp. 1-8.
Wang et al., "Optimization of Butanol Production from Tropical Maize Stalk Juice by Fermentation with *Clostridium beijerinckii* NCIMB 8052", Bioresource Technology, vol. 102, Aug. 2011, pp. 9985-9990.
Huang et al., "Acetic Acid Production from Fructose by *Clostridium formicoaceticum* Immobilized in a Fibrous-bed Bioreactor", Biotechnology Process, vol. 14, 1998, pp. 800-806.
Rodriguez et al., "Mannitol Production by Heterofermentative *Lactobacillus reuteri* CRL 1101 and *Lactobacillus fermentum* CRL 573 in Free and Controlled pH Batch Fermentations", Applied Microbiology and Biotechnology, vol. 93, Oct. 2011, pp. 2519-2527.
Yu et al., "Selective Utilization of Fructose to Glucose by *Candida magnoliae*, an Erythritol Producer", Applied Biochemistry and Biotechnology, vol. 129-132, 2006, pp. 870-879.
Al-Shorgani et al., "The Effect of Different Carbon Sources on Biobutanol Production Using *Clostridium saccharoperbutylacetonicum* N1-4", Biotechnology, vol. 10, 2011, pp. 280-285.
Ferchichi et al., "Influence of Culture Parameters on Biological Hydrogen Production by *Clostridium saccharoperbutylacetonicum* ATCC 27021", World Journal of Microbiology & Biotechnology, vol. 21, 2005, pp. 855-862.
Ye Ni et al., "Butanol Fermentation from Low-Value Sugar-Based Feedstocks by Clostridia", Conference presentation/*Clostridium* XII, Sep. 2012, Nottingham, UK, Sep. 2012, pp. 1-23—http://www.clostridia.net/clostridiumXII/clostridium-xii-talks/NI.pdf—retrieved Mar. 13, 2013.
Database Medline [Online] US National Library of Medicine (NLM), Bethesda, MD, US; Oct. 2011, Deng et al., "Acetone-butanol Fermentation from the Mixture of Fructose and Glucose (in Chinese)".

* cited by examiner

*Primary Examiner* — Allison Fox
*Assistant Examiner* — Yvonne Pyla
(74) *Attorney, Agent, or Firm* — Leber Patent Law P.C.

(57) ABSTRACT

Some products such as solvents, e.g., butanol, are toxic to solvent-producing microorganisms, yet fructose metabolism can facilitate the increase of protective substrates such as triglycerides, which can protect the microorganism from the toxic effect of the product. Methods are provided for producing a product, e.g., a solvent from fructose derived from a cellulosic or lignocellulosic material. Using the methods herein, a fructose solution can be fermented to a solvent more rapidly, and with better yields, than a glucose solution.

17 Claims, 5 Drawing Sheets

PROCESSING BIOMASS

CROSS-REFERENCE TO RELATED APPLICATION

This application is a continuation of PCT/US2012/071097, filed Dec. 20, 2012, which claimed priority from U.S. Provisional Application Nos. 61/579,552 and 61/579,559 both filed on Dec. 22, 2011. The entire disclosures of the above applications are incorporated herein by reference.

FIELD OF THE INVENTION

The invention pertains to methods of converting biomass to useful products. In particular, the inventions relates to the production of products, such as butanol from sugars, such as fructose.

BACKGROUND

As demand for petroleum increases, so too does interest in renewable feedstocks for manufacturing biofuels and biochemicals. The use of lignocellulosic biomass as a feedstock for such manufacturing processes has been studied since the 1970s. Lignocellulosic biomass is attractive because it is abundant, renewable, domestically produced, and does not compete with food industry uses.

Many potential lignocellulosic feedstocks are available today, including agricultural residues, woody biomass, municipal waste, oilseeds/cakes and sea weeds, to name a few. At present these materials are either used as animal feed, biocompost materials, are burned in a cogeneration facility or are landfilled.

Lignocellulosic biomass is recalcitrant to degradation as the plant cell walls have a structure that is rigid and compact. The structure comprises crystalline cellulose fibrils embedded in a hemicellulose matrix, surrounded by lignin. This compact matrix is difficult to access by enzymes and other chemical, biochemical and biological processes. Cellulosic biomass materials (e.g., biomass material from which substantially all the lignin has been removed) can be more accessible to enzymes and other conversion processes, but even so, naturally-occurring cellulosic materials often have low yields (relative to theoretical yields) when contacted with hydrolyzing enzymes. Lignocellulosic biomass is even more recalcitrant to enzyme attack. Furthermore, each type of lignocellulosic biomass has its own specific composition of cellulose, hemicellulose and lignin.

While a number of methods have been tried to extract structural carbohydrates from lignocellulosic biomass, they are either too expensive, produce too low a yield, leave undesirable chemicals in the resulting product, or simply degrade the sugars.

Monosaccharides from renewable biomass sources could become the basis of chemical and fuels industries by replacing, supplementing or substituting petroleum and other fossil feedstocks. However, techniques need to be developed that will make these monosaccharides available in large quantities and at acceptable purities and prices.

SUMMARY OF THE INVENTION

Provided herein are methods of increasing the efficiency of saccharification of biomass. In particular, efficiencies can be achieved by avoiding negative feedback inhibition of enzymatic reactions.

In one aspect, the invention features a method for producing a product, the method comprising: producing fructose by saccharifying a biomass and contacting the saccharifed biomass with an isomerization agent, and converting the fructose to a product with a microorganism and/or an enzyme.

In some implementations, the biomass comprises a cellulosic or lignocellulosic material. The cellulosic or lignocellulosic biomass is treated to reduce its recalcitrance to saccharification, for example, using a treatment method selected from the group consisting of: bombardment with electrons, sonication, oxidation, pyrolysis, steam explosion, chemical treatment, mechanical treatment, freeze grinding and combination thereof.

The isomerization agent may be, for example, an isomerase, e.g., xylose isomerase.

In some implementations, the cellulosic or lignocellulosic biomass is selected from the group consisting of: paper, paper products, paper waste, paper pulp, pigmented papers, loaded papers, coated papers, filled papers, magazines, printed matter, printer paper, polycoated paper, card stock, cardboard, paperboard, cotton, wood, particle board, forestry wastes, sawdust, aspen wood, wood chips, grasses, switchgrass, miscanthus, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, manure, sewage, arracacha, buckwheat, banana, barley, cassava, kudzu, oca, sago, sorghum, potato, sweet potato, taro, yams, beans, favas, lentils, peas, industrial waste, and mixtures of any of these.

In some cases, the microorganism comprises a strain of *Clostridium* spp. For example, the microorganism may be *C. saccharoperbutylacetonicum*, e.g., *C. saccharoperbutylacetonicum* strain ATCC 27021 or *C. saccharoperbutylacetonicum* strain ATCC 27022.

The product may comprise a solvent, e.g., an alcohol such as isobutanol or n-butanol.

In some embodiments described herein, while it is generally preferred that products such as butanol be produced from sugars, such as fructose, that is derived from a cellulosic or lignocellulosic material, fructose from other sources may be used.

It should be understood that this invention is not limited to the embodiments disclosed in this Summary, and it is intended to cover modifications that are within the spirit and scope of the invention, as defined by the claims.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

This invention relates to methods of processing biomass materials (e.g., biomass materials or biomass-derived materials) to obtain sugars such as fructose that can then be utilized to produce a product. For example, sugars, e.g. fructose, can be fermented to produce a solvent, such as an alcohol, for example butanol, e.g., isobutanol or n-butanol. Butyric acid can also be produced. The inventors have found that in some cases a fructose solution can be fermented to an alcohol more rapidly, and with better yields, than a glucose solution.

Without being bound to any particular theory, it is believed that products, such as solvents (e.g., butanol), are toxic to solvent-producing organisms, and that metabolism with some sugars such as fructose produce protective substrates (e.g., triglycerides), to a greater degree or faster than glucose metabolism. A suggested effect of solvents is that they interact with cell membranes disrupting membrane fluidity. Solvents, such as butanol are also attributed to have a chaotropic effect on the membrane. Chaotropic agents interfere with stabilizing intramolecular interactions mediated by non-covalent forces. Due to these effects, solvents can inhibit active nutrient transport, the activity of membrane-bound enzymes, and glucose uptake. Solvents can also partially or completely abolish the membrane pH gradient, lower intracellular pH and ATP concentrations. In response to increasing solvents, the cells may attempt to adjust lipid composition to maintain fluidity (Christopher A. Tomas, *J. Bacteriol.* 186:2006-2018 (2004)). Fructose metabolism can facilitate the increase of lipids such as triglycerides.

Without being bound to any particular theory, it is further believed that the benefit of sugars such as fructose for solvent production may be related to regulation of glycolysis. The purpose of regulation is to control the growth and health of the organism. It is believed that since some sugars such as fructose are not as naturally abundant in the world as glucose is, the regulation mechanism for suppressing its glycolysis is not as well developed. This can allow a higher intake and metabolism of those sugars such as fructose by an organism.

Figure 1:
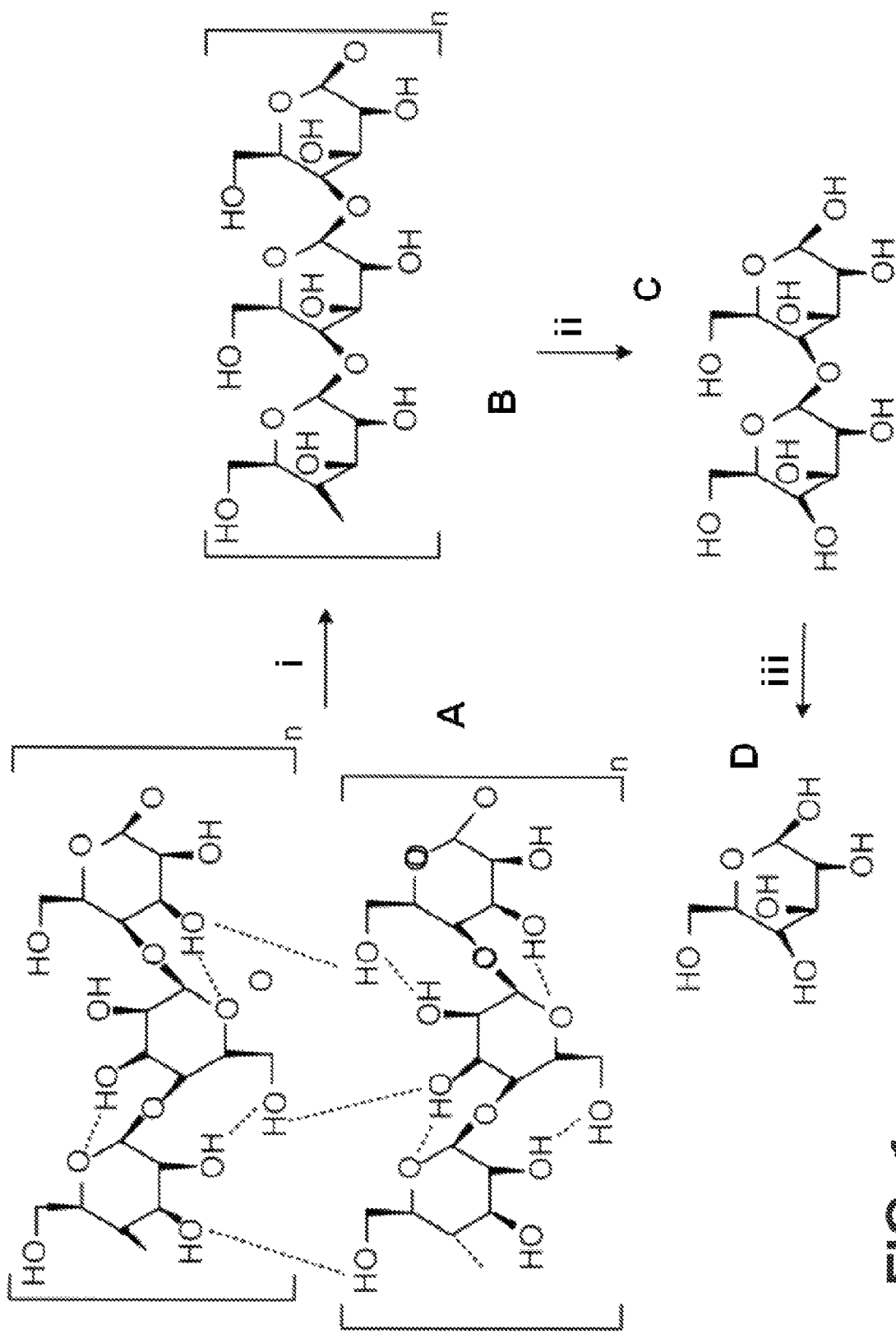
FIG. 1 is a diagram illustrating enzymatic hydrolysis of cellulose to glucose. Cellulosic substrate (A) is converted by endocellulase (i) to cellulose (B), which is converted by exocellulase (ii) to cellobiose (C), which is converted to glucose (D) by cellobiase (beta-glucosidase) (iii).

As shown in FIG. 1, for example, during saccharification a cellulosic substrate (A) is initially hydrolyzed by endoglucanases (i) at random locations producing oligomeric intermediates (e.g., cellulose) (B). These intermediates are then substrates for exo-splitting glucanases (ii) such as cellobiohydrolase to produce cellobiose from the ends of the cellulose polymer. Cellobiose is a water-soluble 1,4-linked dimer of glucose. Finally cellobiase (iii) cleaves cellobiose (C) to yield glucose (D). Therefore, the endoglucanases are particularly effective in attacking the crystalline portions of cellulose and increasing the effectiveness of exocellulases to produce cellobiose, which then requires the specificity of the cellobiose to produce glucose. Therefore, it is evident that depending on the nature and structure of the cellulosic substrate, the amount and type of the three different enzymes may need to be modified.

Figure 2:
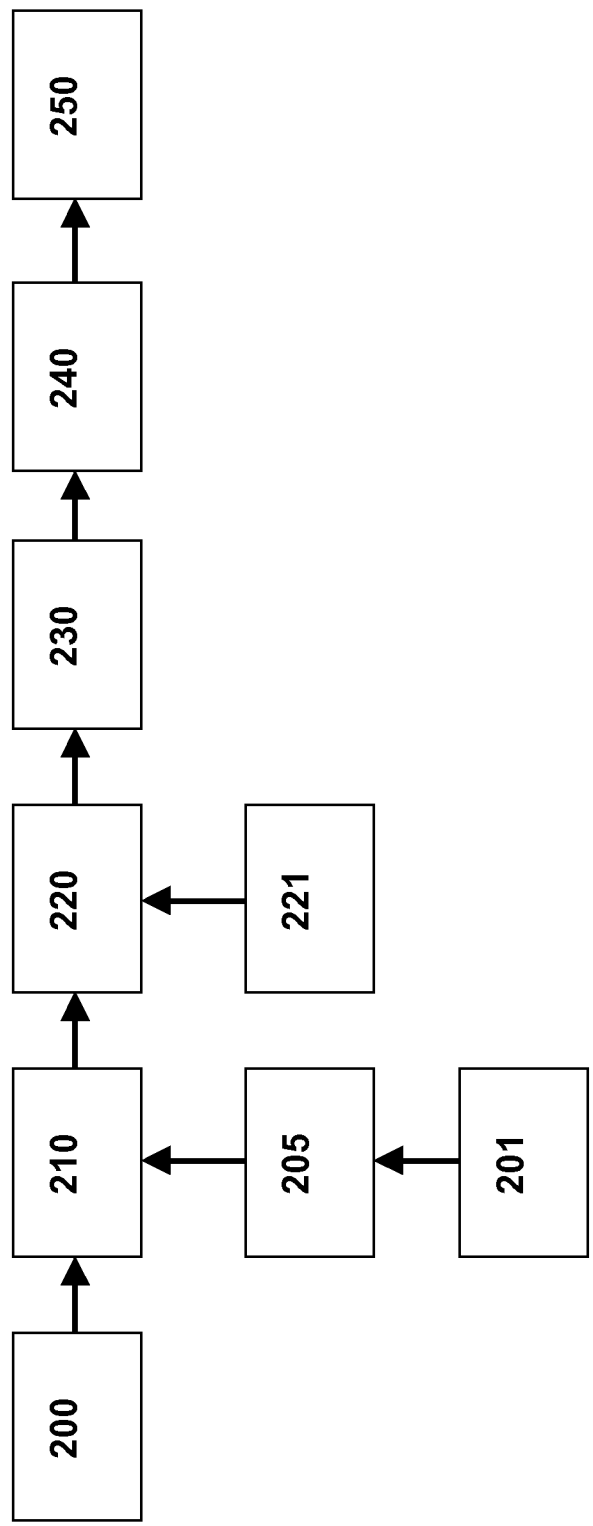
FIG. 2 is a flow diagram illustrating conversion of a biomass feedstock to one or more products. Feedstock is physically pretreated (e.g., to reduce its size) (200), optionally treated to reduce its recalcitrance (210), saccharified to form a sugar solution (220), the solution is transported (230) to a manufacturing plant (e.g., by pipeline, railcar) (or if saccharification is performed en route, the feedstock, enzyme and water is transported), the saccharified feedstock is bio-processed to produce a desired product (e.g., alcohol) (240), and the product can be processed further, e.g., by distillation, to produce a final product (250). Treatment for recalcitrance can be modified by measuring lignin content (201) and setting or adjusting process parameters (205). Saccharifying the feedstock (220) can be modified by mixing the feedstock with medium and the enzyme (221).

A process for manufacturing an alcohol, e.g., butanol, is shown in FIG. 2. A process for manufacturing an alcohol can include, for example, optionally mechanically treating a feedstock, e.g., to reduce its size (200), before and/or after this treatment, optionally treating the feedstock with another physical treatment to further reduce its recalcitrance (210), then saccharifying the feedstock, using the enzyme complex, to form a sugar solution (220). Optionally, the method may also include transporting, e.g., by pipeline, railcar, truck or barge, the solution (or the feedstock, enzyme and water, if saccharification is performed en route) to a manufacturing plant (230). In some cases the saccharified feedstock is further bioprocessed (e.g., fermented) to produce a desired product e.g., alcohol (240). This resulting product may in some implementations be processed further, e.g., by distillation (250), to produce a final product. One method of reducing the recalcitrance of the feedstock is by electron bombardment of the feedstock. If desired, the steps of measuring lignin content of the feedstock (201) and setting or adjusting process parameters based on this measurement (205) can be performed at various stages of the process, as described in U.S. Pat. App. Pub. 2010/0203495 A1 by Medoff and Masterman, published Aug. 12, 2010, the complete disclosure of which is incorporated herein by reference. Saccharifying the feedstock (220) can also be modified by mixing the feedstock with medium and the enzyme (221).

The method steps discussed above with reference to FIG. 2 will now be discussed in further detail, followed by a discussion of the materials used in the process.

Fermentation of Fructose to Useful Products

The fructose solution produced by saccharification or saccharification followed by isomerization can be fermented to produce an alcohol, e.g., butanol, or butyric acid.

Figure 3:
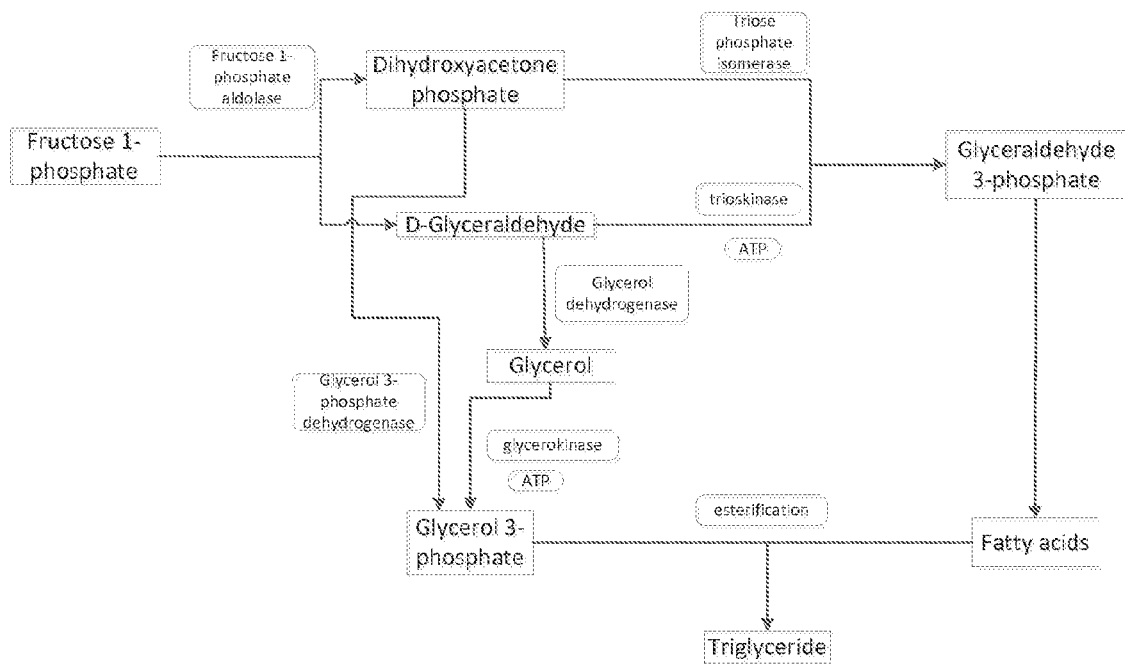
FIG. 3 is a diagram showing the preparatory phase of the metabolism of glucose and fructose.

FIG. 3 shows the preparatory phase of glycolysis for both fructose and glucose. Fermentation includes a multiphase glycolysis reaction, the preparatory phase of which produces glyceraldehyde 3-phosphate. As shown in FIG. 3 and discussed in detail below, production of glyceraldehyde 3-phosphate from fructose involves fewer reactions than production from glucose, which may contribute to the greater efficiency observed with fructose fermentation as compared to glucose fermentation.

Referring to the glucose pathway in FIG. 3, glucose is converted to glucose 6-phosphate by the action of hexokinase with ATP. Glucose 6-phosphate is then isomerized to fructose 6-phosphate by phosphohexoisomerase and then is further converted to fructose 1,6-phosphate by the action of phophofructokinase and ATP. At this point, the diphosphated sugar is split by fructose bisphosphate aldolase into dihydroxyacetone phosphate and glyceraldehyde 3-phosphate. The dihydroxyacetone phosphate is isomerized to glyceraldehyde 3-phosphate by the action of triose phosphate isomerase.

Referring again to FIG. 3, there are several paths for glycolysis of fructose. While hexokinase reacts strongly with glucose, its affinity for fructose is low. Therefore, although fructose can be phosphorylated to glucose 6-phosphate by hexokinase and ATP, it is expected that the contribution to glycolysis by this pathway is quite low. The more likely path starts with the phosphorylation of fructose by the action of fructokinase and ATP, giving fructose 1-phosphate. Fructose 1-phosphate is then split into dihydroxyacetone phosphate and D-glyceraldehyde by fructose 1-phosphate aldolase. As in the glucose pathway, dihydroxyacetone phosphate is isomerized to glyceraldehyde 3-phosphate by triose phosphate isomerase. The D-glyceraldehyde is converted to the glyceraldehyde 3-phosphate by trioskinase and ATP.

The microorganism used in fermentation is preferably selected to produce butanol e.g., isobutanol or n-butanol. Suitable microorganisms include those discussed in the Materials section, below. Many butanol-producing organisms are obligate anaerobes.

Figure 4:
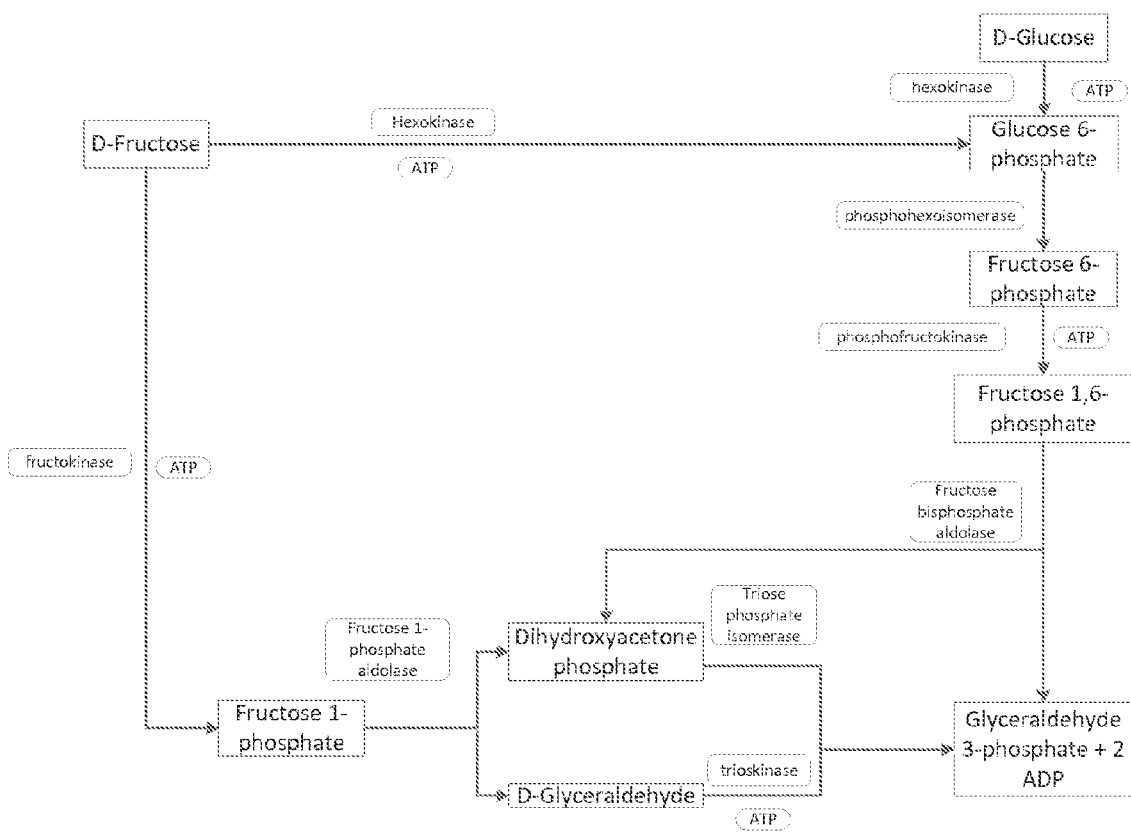
FIG. 4 is a diagram showing a metabolic pathway for the formation of triglycerides during metabolism of fructose.

Fructose can drive the production of triglycerides as a by-product of glycolysis, as shown in FIG. 4. The final step shown in FIG. 4 for the formation of triglycerides involves an esterification between glycerol 3-phosphate and fatty acids. Fatty acids are formed from glyceraldehyde 3-phosphate, the formation of which has been described above, with multiple intermediates not shown here. The formation of glycerol 3-phosphate is shown in FIG. 4 and can occur from the action of glycerol 3-phosphate dehydrogenase on dihydroxyacetone phosphate. This can also occur through the action of glycerol dehydrogenase on D-glyceraldehyde, forming glycerol, which is then phosphorylated with glycerokinase and ATP to glycerol 3-phosphate. Although the formation of glycerol 3-phosphate is possible from glucose through the dihydroxyacetone phosphate intermediate, the additional pathway through D-glycerolaldehyde, which is only available through fructose can produce more of this intermediate. The triglycerides produced by esterification of the glycerol 3-phosphate may help in the production of butanol by protecting the butanol-producing organism from the toxic effects of butanol.

Figure 5:
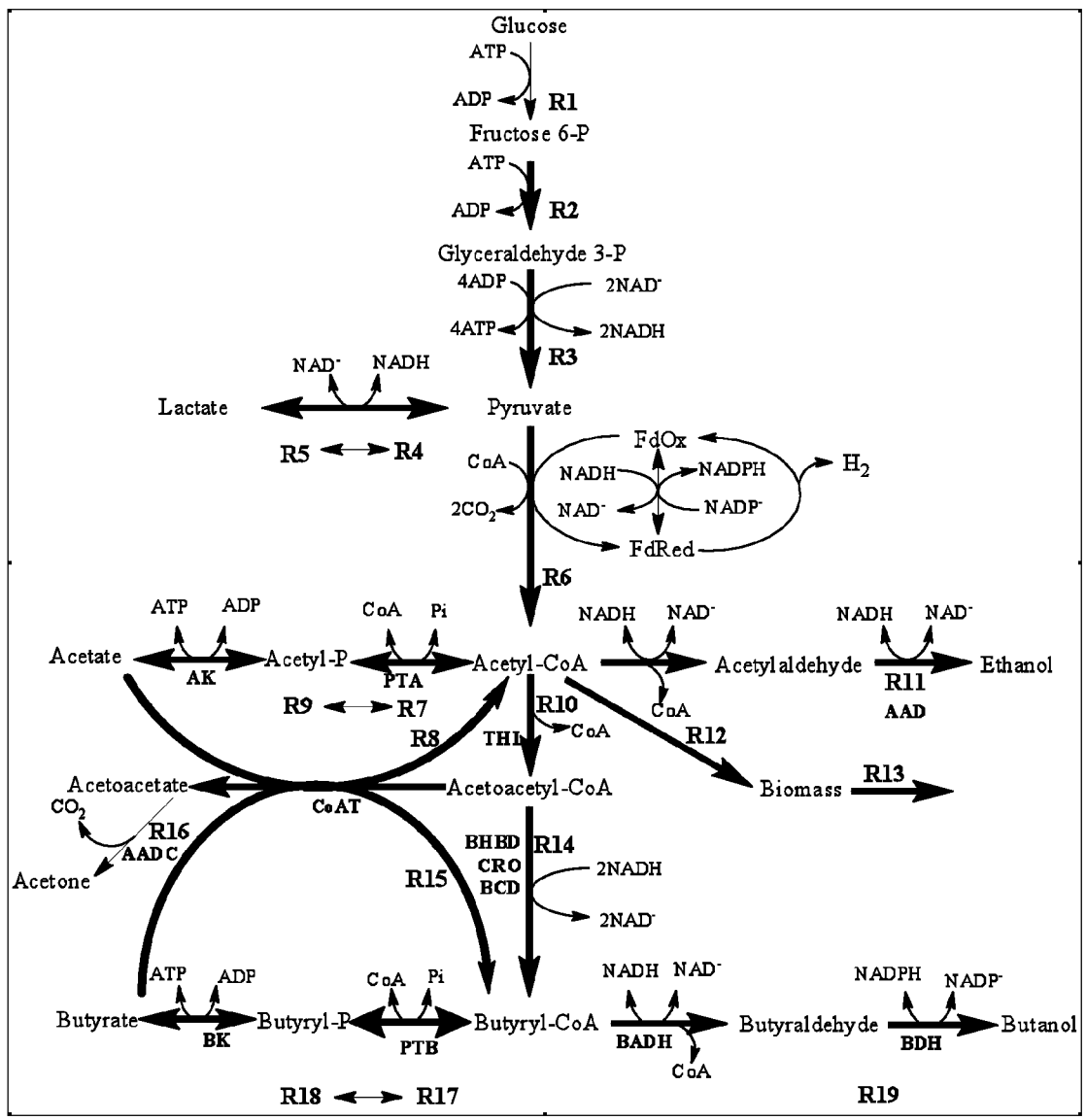
FIG. 5 is a diagram showing a fermentative pathway for a butanol-producing organism.

FIG. 5 shows a fermentative pathway for a butanol-producing organism (*Clostridium acetobutylicium*). In a typical fermentation, after an induction period, the cells enter an exponential growth phase. In the growth phase, butyrate and acetate are first produced, along with ATP needed for cell growth. This phase is also called the acidogenesis phase. Approaching, and in the stationary phase, the culture undergoes a metabolic shift towards the formation of acetone, butanol and ethanol as main solvent products. This stage is also known as the solventogenic phase. During and after the solventogenic phase the cells will become vegetative, die and/or sporulate. In FIG. 5 reactions are represented by bold arrows and denoted by symbols from R1 to R19. The acidogenic reactions are R9 and R18 (catalyzed by PTA-AK and PTB-BK, respectively), generating acetate and butyrate respectively. The two acids are reassimilated through R7 and R17 (the reverse paths of R9 and R18), or directly converted to acetyl-CoA and butyryl-CoA through R8 and R15 (catalyzed by CoAT). The solventogenic reactions are R11, R16 and R19 (catalyzed by AAD, AADC and BDH, respectively), generating ethanol, acetate and butanol respectively. R14 is a lumped reaction consisting of reactions catalyzed by BHBD, CRO and BCD (http://www.biomedcentral.com/1752-0509/5/S1/S12 "An improved kinetic model for the acetone-butanol-ethanol pathways of *Clostridium acetobutylicum* and model-based perturbation analysis").

The optimum pH for fermentation is from about pH 4 to 7. Typical fermentation times are about 24 to 168 hours with temperatures in the range of 20° C. to 40° C., however thermophilic microorganisms prefer higher temperatures. For anaerobic organisms it is preferable to conduct the fermentation in the absence of oxygen e.g., under a blanket of an inert gas such as $N_2$, Ar, He, $CO_2$ or mixtures thereof. Additionally, the mixture may have a constant purge of an inert gas flowing through the tank during part of or all of the fermentation.

Jet mixing or other agitation may be used during fermentation, and in some cases saccharification and fermentation are performed in the same tank. In some embodiments, the fermentation is done without any mechanical mixing.

Nutrients may be added during saccharification and/or fermentation, for example, the food-based nutrient packages described in U.S. Ser. No. 13/184,138 and U.S. Pat. No. 6,358,717 the complete disclosure of which is incorporated herein by reference.

Mobile fermentors can be utilized, as described in U.S. Pat. No. 8,318,453. Similarly, the saccharification equipment can be mobile. Further, saccharification and/or fermentation may be performed in part or entirely during transit.

Preferred Fermentation Agents

The microorganism(s) used in fermentation can be naturally-occurring microorganisms and/or engineered microorganisms. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

Suitable fermenting microorganisms have the ability to convert fructose and preferably also other sugars, such as glucose, xylose, arabinose, mannose, galactose, oligosaccharides or polysaccharides, into an alcohol, e.g., butanol or a butanol derivative.

Exemplary microorganisms include, but are not limited to, the following strains of *Clostridium*:

TABLE 1

Exemplary strains of *Clostridium*

| | |
|---|---|
| C. saccharoperbutylacetonicum | ATCC 27021 |
| C. saccharoperbutylacetonicum | ATCC 27022 |
| C. saccharobutylicum | ATCC BAA-117 |
| C. puniceum | ATCC 43978 |
| C. beijernckii | ATCC 6014 |
| C. acetobutylicum | NRRL B-527 |
| C. acetobutylicum | NRRL B-591 |
| C. beijerinckii | NRRL B593 |
| C. acetobutylicum | NRRL B-596 |
| C. beijernckii | ATCC 11914 |
| C. acetobutylicum | DSM 1732 |
| C. beijerinckii | NRRL B-592 |
| C. acetobutylicum | ATCC 3625 |
| C. saccharobutylicum | NRRL B-643 |
| C. acetobutylicium | NRRL B595 |
| C. roseum | NRRL 17797 |
| C. actobutylicum | ATCC 4259 |
| C. aurantibutyricum | DSM 793 |
| C. beijerinckii | ATCC 309058 |
| C. felsineum | ATCC 17788 |
| C. saccharobutylicum | NRRL B-643 |

Xylose Isomerase

Xylose isomerase (ES 5.3.1.5) is an enzyme the catalyzes the chemical reaction back and forth between D-xylose and D-xylulose. It is also known systematically as glucose isomerase and D-xylose aldose-ketose isomerase, and belongs to a family of isomerases, specifically those intramolecular oxidoreductases interconverting aldoses and ketoses. Other names in common use include D-xylose isomerase, D-xylose ketoisomerase, and D-xylose ketol-isomerase. The enzyme participates in pentose and glucuronate interconversions and fructose and mannose metabolism. It is used industrially to convert glucose to fructose in the manufacture of high-fructose corn syrup. It is sometimes referred to as "glucose isomerase." "Xylose isomerase" and "glucose isomerase" are used interchangeably herein. In vitro, glucose isomerase catalyzes the interconversion of glucose and fructose. In vivo, it catalyzes the interconversion of xylose and xylulose.

Several types of enzymes are considered xylose isomerases. The first kind is produced from *Pseudomonas hydrophila*. This enzyme has 160 times lower affinity to glucose than xylose but nonetheless is useful for increasing the amount of fructose in the presence of glucose. A second kind of enzyme is found in *Escherichia intermedia*. This enzyme is a phophoglucose isomerase (EC 5.3.1.9) and can isomerize unphosphorylated sugar only in the presence of arsenate. A glucose isomerase (EC 5.3.16) can be isolated from *Bacillus megaterium* AI and is NAD linked and is specific to glucose. Another glucose isomerase having similar activity is isolated from *Paracolobacterium aerogenoides*. Glucose isomerases produced by heterolactic acid bacteria require xylose as an inducer and are relatively unstable at high temperature. The xylose isomerase (EC 5.3.1.5) is the most useful for commercial applications as it does not require expensive cofactors such as NAD+ or ATP and it is relatively heat stable.

The glucose isomerases are usually produced intercellularly but reports of extracellular secretion of glucose isomerases are known. The enzyme used can be isolated from many bacteria including but not limited to: *Actinomyces olivocinereus, Actinomyces phaeochromogenes, Actinoplanes missouriensis, Aerobacter aerogenes, Aerobacter cloacae, Aerobacter levanicum, Arthrobacter* spp., *Bacillus stearothermophilus, Bacillus megabacterium, Bacillus coagulans, Bifidobacterium* spp., *Brevibacterium incertum, Brevibacterium pentosoaminoacidicum, Chainia* spp., *Corynebacterium* spp., *Cortobacterium helvolum, Escherichia freundii, Escherichia intermedia, Escherichia coli, Flavobacterium arborescens, Flavobacterium devorans, Lactobacillus brevis, Lactobacillus buchneri, Lactobacillus fermenti, Lactobacillus mannitopoeus, Lactobacillus gayonii, Lactobacillus plantarum, Lactobacillus lycopersici, Lactobacillus pentosus, Leuconostoc mesenteroides, Microbispora rosea, Microellobosporia flavea, Micromonospora coerula, Mycobacterium* spp., *Nocardia asteroides, Nocardia corallia, Nocardia dassonvillei, Paracolobacterium aerogenoides, Pseudonocardia* spp., *Pseudomonas hydrophila, Sarcina* spp., *Staphylococcus bibila, Staphylococcus flavovirens, Staphylococcus echinatus, Streptococcus achromogenes, Streptococcus phaeochromogenes, Streptococcus fracliae, Streptococcus roseochromogenes, Streptococcus olivaceus, Streptococcus californicos, Streptococcus venuceus, Streptococcus virginial, Streptomyces olivochromogenes, Streptococcus venezaelie, Streptococcus wedmorensis, Streptococcus griseolus, Streptococcus glaucescens, Streptococcus bikiniensis, Streptococcus rubiginosus, Streptococcus achinatus, Streptococcus cinnamonensis, Streptococcus fradiae, Streptococcus albus, Streptococcus griseus, Streptococcus hivens, Streptococcus matensis, Streptococcus murinus, Streptococcus nivens, Streptococcus platensis, Streptosporangium album, Streptosporangium oulgare, Thermopolyspora* spp., *Thermus* spp., *Xanthomonas* spp. and *Zymononas mobilis*.

Glucose isomerase can be used free in solution or immobilized on a support to convert glucose to fructose. Whole cells or cell free enzymes can be immobilized. The support structure can be any insoluble material. Support structures can be cationic, anionic or neutral materials, for example diethylaminoethyl cellulose, metal oxides, metal chlorides, metal carbonates and polystyrenes. Immobilization can be accomplished by any suitable means. For example, immobilization can be accomplished by contacting the support and the whole cell or enzyme in a solvent such as water and then removing the solvent. The solvent can be removed by any suitable means, for example filtration or evaporation or spray drying. As another example, spray drying the whole cells or enzyme with a support can be effective.

Glucose isomerase can also be present in a living cell that produces the enzyme during the process. For example, a glucose isomerase producing bacteria can be co-cultured in the process with an ethanol fermenting bacteria. Alternatively, the glucose-isomerase-producing bacteria can be first contacted with the substrate, followed by inoculating with an ethanol-producing substrate.

Glucose isomerase can also be present within or secreted from a cell also capable of a further useful transformation of sugars. For example, a glucose fermenting species can be genetically modified to contain and express the gene for production of glucose isomerase.

Isolation of Solvents

After fermentation, the resulting fluids can be purified using any useful method. For example, some useful methods are distillation, adsorption, liquid-liquid extraction, perstraction, reverse osmosis, pervaporation and gas stripping (see, e.g., *J. Ind. Microbiol. Biotechnol.* (2009) 36:1127-1138).

Biomass Materials

As used herein, the term "biomass materials" includes lignocellulosic, cellulosic, starchy, and microbial materials.

Lignocellulosic materials include, but are not limited to, wood, particle board, forestry wastes (e.g., sawdust, aspen wood, wood chips), grasses, (e.g., switchgrass, miscanthus, cord grass, reed canary grass), grain residues, (e.g., rice hulls, oat hulls, wheat chaff, barley hulls), agricultural waste (e.g., silage, canola straw, wheat straw, barley straw, oat straw, rice straw, jute, hemp, flax, bamboo, sisal, abaca, corn cobs, corn stover, soybean stover, corn fiber, alfalfa, hay, coconut hair), sugar processing residues (e.g., bagasse, beet pulp, agave bagasse), seaweed, manure, sewage, and mixtures of any of these.

In some cases, the lignocellulosic material includes corncobs. Ground or hammermilled corncobs can be spread in a layer of relatively uniform thickness for irradiation, and after irradiation are easy to disperse in the medium for further processing. To facilitate harvest and collection, in some cases the entire corn plant is used, including the corn stalk, corn kernels, and in some cases even the root system of the plant.

Advantageously, no additional nutrients (other than a nitrogen source, e.g., urea or ammonia) are required during fermentation of corncobs or cellulosic or lignocellulosic materials containing significant amounts of corncobs.

Corncobs, before and after comminution, are also easier to convey and disperse, and have a lesser tendency to form explosive mixtures in air than other cellulosic or lignocellulosic materials such as hay and grasses.

Cellulosic materials include, for example, paper, paper products, paper waste, paper pulp, pigmented papers, loaded papers, coated papers, filled papers, magazines, printed matter (e.g., books, catalogs, manuals, labels, calendars, greeting cards, brochures, prospectuses, newsprint), printer paper, polycoated paper, card stock, cardboard, paperboard, materials having a high α-cellulose content such as cotton, and mixtures of any of these. For example, paper products as described in U.S. App. No. 2013/0052687 ("Magazine Feedstocks" by Medoff et al., filed Feb. 14, 2012), the full disclosure of which is incorporated herein by reference.

Cellulosic materials can also include lignocellulosic materials which have been de-lignified.

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials. Mixtures of starchy, cellulosic and or lignocellulosic materials can also be used. For example, a biomass can be an entire plant, a part of a plant or different parts of a plant, e.g., a wheat plant, cotton plant, a corn plant, rice plant or a tree. The starchy materials can be treated by any of the methods described herein.

Microbial materials include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture and fermentation systems.

The biomass material can also include offal, and similar sources of material.

In other embodiments, the biomass materials, such as cellulosic, starchy and lignocellulosic feedstock materials, can be obtained from transgenic microorganisms and plants that have been modified with respect to a wild type variety. Such modifications may be, for example, through the iterative steps of selection and breeding to obtain desired traits in a plant. Furthermore, the plants can have had genetic material removed, modified, silenced and/or added with respect to the wild type variety. For example, genetically modified plants can be produced by recombinant DNA methods, where genetic modifications include introducing or modifying specific genes from parental varieties, or, for example, by using transgenic breeding wherein a specific gene or genes are introduced to a plant from a different species of plant and/or bacteria. Another way to create genetic variation is through mutation breeding wherein new alleles are artificially created from endogenous genes. The artificial genes can be created by a variety of ways including treating the plant or seeds with, for example, chemical mutagens (e.g., using alkylating agents, epoxides, alkaloids, peroxides, formaldehyde), irradiation (e.g., X-rays, gamma rays, neutrons, beta particles, alpha particles, protons, deuterons, UV radiation) and temperature shocking or other external stressing and subsequent selection techniques. Other methods of providing modified genes is through error prone PCR and DNA shuffling followed by insertion of the desired modified DNA into the desired plant or seed. Methods of introducing the desired genetic variation in the seed or plant include, for example, the use of a bacterial carrier, biolistics, calcium phosphate precipitation, electroporation, gene splicing, gene silencing, lipofection, microinjection and viral carriers. Additional genetically modified materials have been described in U.S. application Serial No 2012/0052682 filed Feb. 14, 2012 the full disclosure of which is incorporated herein by reference.

Any of the methods described herein can be practiced with mixtures of any biomass materials described herein.

Biomass Material Preparation—Mechanical Treatments

The biomass can be in a dry form, for example with less than about 35% moisture content (e.g., less than about 20%, less than about 15%, less than about 10% less than about 5%, less than about 4%, less than about 3%, less than about 2% or even less than about 1%). The biomass can also be delivered in a wet state, for example as a wet solid, a slurry or a suspension with at least about 10 wt % solids (e.g., at least about 20 wt. %, at least about 30 wt. %, at least about 40 wt. %, at least about 50 wt. %, at least about 60 wt. %, at least about 70 wt. %).

The processes disclosed herein can utilize low bulk density materials, for example cellulosic or lignocellulosic feedstocks that have been physically pretreated to have a bulk density of less than about 0.75 g/cm$^3$, e.g., less than about 0.7, 0.65, 0.60, 0.50, 0.35, 0.25, 0.20, 0.15, 0.10, 0.05 or less, e.g., less than about 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters. If desired, low bulk density materials can be densified, for example, by methods described in U.S. Pat. No. 7,971,809 to Medoff, the full disclosure of which is hereby incorporated by reference.

In some cases, the pre-treatment processing includes screening of the biomass material. Screening can be through a mesh or perforated plate with a desired opening size, for example, less than about 6.35 mm (¼ inch, 0.25 inch), (e.g., less than about 3.18 mm (⅛ inch, 0.125 inch), less than about 1.59 mm (1/16 inch, 0.0625 inch), is less than about 0.79 mm (1/32 inch, 0.03125 inch), e.g., less than about 0.51 mm (1/50 inch, 0.02000 inch), less than about 0.40 mm (1/64 inch, 0.015625 inch), less than about 0.23 mm (0.009 inch), less than about 0.20 mm (1/128 inch, 0.0078125 inch), less than about 0.18 mm (0.007 inch), less than about 0.13 mm (0.005 inch), or even less than about 0.10 mm (1/256 inch, 0.00390625 inch)). In one configuration, the desired biomass falls through the perforations or screen and thus biomass larger than the perforations or screen are not irradiated. These larger materials can be re-processed, for example by comminuting, or they can simply be removed from processing. In another configuration material that is larger than the perforations is irradiated and the smaller material is removed by the screening process or recycled. In this kind of a configuration, the conveyor itself (for example a part of the conveyor) can be perforated or made with a mesh. For example, in one particular embodiment the biomass material may be wet and the perforations or mesh allow water to drain away from the biomass before irradiation.

Screening of material can also be by a manual method, for example by an operator or mechanoid (e.g., a robot equipped with a color, reflectivity or other sensor) that removes unwanted material. Screening can also be by magnetic screening wherein a magnet is disposed near the conveyed material and the magnetic material is removed magnetically.

Optional pre-treatment processing can include heating the material. For example, a portion of the conveyor can be sent through a heated zone. The heated zone can be created, for example, by IR radiation, microwaves, combustion (e.g., gas, coal, oil, biomass), resistive heating and/or inductive coils. The heat can be applied from at least one side or more than one side, can be continuous or periodic and can be for only a portion of the material or all the material. For example, a portion of the conveying trough can be heated by use of a heating jacket. Heating can be, for example, for the purpose of drying the material. In the case of drying the material, this can also be facilitated, with or without heating, by the movement of a gas (e.g., air, oxygen, nitrogen, He, $CO_2$, Argon) over and/or through the biomass as it is being conveyed.

Optionally, pre-treatment processing can include cooling the material. Cooling material is described in U.S. Pat. No. 7,900,857 to Medoff, the disclosure of which in incorporated herein by reference. For example, cooling can be by supplying a cooling fluid, for example water (e.g., with glycerol), or nitrogen (e.g., liquid nitrogen) to the bottom of the conveying trough. Alternatively, a cooling gas, for example, chilled nitrogen can be blown over the biomass materials or under the conveying system.

Another optional pre-treatment processing method can include adding a material to the biomass. The additional material can be added by, for example, by showering, sprinkling and or pouring the material onto the biomass as it is conveyed. Materials that can be added include, for example, metals, ceramics and/or ions as described in U.S. Pat. App. Pub. 2010/0105119 A1 (filed Oct. 26, 2009) and U.S. Pat. App. Pub. 2010/0159569 A1 (filed Dec. 16, 2009), the entire disclosures of which are incorporated herein by reference. Optional materials that can be added include acids and bases. Other materials that can be added are oxidants (e.g., peroxides, chlorates), polymers, polymerizable monomers (e.g., containing unsaturated bonds), water, catalysts, enzymes and/or organisms. Materials can be added, for example, in pure form, as a solution in a solvent (e.g., water or an organic solvent) and/or as a solution. In some cases the solvent is volatile and can be made to evaporate e.g., by heating and/or blowing gas as previously described. The added material may form a uniform coating on the biomass or be a homogeneous mixture of different components (e.g., biomass and additional material). The added material can modulate the subsequent irradiation step by increasing the efficiency of the irradiation, damping the irradiation or changing the effect of the irradiation (e.g., from electron beams to X-rays or heat). The method may have no impact on the irradiation but may be useful for further downstream processing. The added material may help in conveying the material, for example, by lowering dust levels.

Biomass can be delivered to the conveyor by a belt conveyor, a pneumatic conveyor, a screw conveyor, a hopper, a pipe, manually or by a combination of these. The biomass can, for example, be dropped, poured and/or placed onto the conveyor by any of these methods. In some embodiments the material is delivered to the conveyor using an enclosed material distribution system to help maintain a low oxygen atmosphere and/or control dust and fines. Lofted or air suspended biomass fines and dust are undesirable because these can form an explosion hazard or damage the window foils of an electron gun (if such a device is used for treating the material).

The material can be leveled to form a uniform thickness between about 0.0312 and 5 inches (e.g., between about 0.0625 and 2.000 inches, between about 0.125 and 1 inches, between about 0.125 and 0.5 inches, between about 0.3 and 0.9 inches, between about 0.2 and 0.5 inches between about 0.25 and 1.0 inches, between about 0.25 and 0.5 inches, 0.100+/−0.025 inches, 0.150+/−0.025 inches, 0.200+/−0.025 inches, 0.250+/−0.025 inches, 0.300+/−0.025 inches, 0.350+/−0.025 inches, 0.400+/−0.025 inches, 0.450+/−0.025 inches, 0.500+/−0.025 inches, 0.550+/−0.025 inches, 0.600+/−0.025 inches, 0.700+/−0.025 inches, 0.750+/−0.025 inches, 0.800+/−0.025 inches, 0.850+/−0.025 inches, 0.900+/−0.025 inches, 0.900+/−0.025 inches.

Generally, it is preferred to convey the material as quickly as possible through the electron beam to maximize throughput. For example, the material can be conveyed at rates of at least 1 ft/min, e.g., at least 2 ft/min, at least 3 ft/min, at least 4 ft/min, at least 5 ft/min, at least 10 ft/min, at least 15 ft/min, 20, 25, 30, 35, 40, 45, 50 ft/min. The rate of conveying is related to the beam current, for example, for a ¼ inch thick biomass and 100 mA, the conveyor can move at about 20 ft/min to provide a useful irradiation dosage, at 50 mA the conveyor can move at about 10 ft/min to provide approximately the same irradiation dosage.

After the biomass material has been conveyed through the radiation zone, optional post-treatment processing can be done. The optional post-treatment processing can, for example, be a process described with respect to the pre-irradiation processing. For example, the biomass can be screened, heated, cooled, and/or combined with additives. Uniquely to post-irradiation, quenching of the radicals can occur, for example, quenching of radicals by the addition of fluids or gases (e.g., oxygen, nitrous oxide, ammonia, liquids), using pressure, heat, and/or the addition of radical scavengers. For example, the biomass can be conveyed out of the enclosed conveyor and exposed to a gas (e.g., oxygen) where it is quenched, forming carboxylated groups. In one embodiment the biomass is exposed during irradiation to the reactive gas or fluid. Quenching of biomass that has been irradiated is described in U.S. Pat. No. 8,083,906 to Medoff, the entire disclosure of which is incorporate herein by reference.

If desired, one or more mechanical treatments can be used in addition to irradiation to further reduce the recalcitrance of the biomass material. These processes can be applied before, during and/or after irradiation.

In some cases, the mechanical treatment may include an initial preparation of the feedstock as received, e.g., size reduction of materials, such as by comminution, e.g., cutting, grinding, shearing, pulverizing or chopping. For example, in some cases, loose feedstock (e.g., recycled paper, starchy materials, or switchgrass) is prepared by shearing or shredding. Mechanical treatment may reduce the bulk density of the biomass material, increase the surface area of the biomass material and/or decrease one or more dimensions of the biomass material.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the structure of the material by mechanical treatment. For example, a feedstock material can be conveyed through ionizing radiation using a conveyor as described herein and then mechanically treated. Chemical treatment can remove some or all of the lignin (for example, chemical pulping) and can partially or completely hydrolyze the material. The methods also can be used with pre-hydrolyzed material. The methods also can be used with material that has not been pre-hydrolyzed The methods can be used with mixtures of hydrolyzed and non-hydrolyzed materials, for example with about 50% or more non-hydrolyzed material, with about 60% or more non-hydrolyzed material, with about 70% or more non-hydrolyzed material, with about 80% or more non-hydrolyzed material or even with 90% or more non-hydrolyzed material.

In addition to size reduction, which can be performed initially and/or later in processing, mechanical treatment can also be advantageous for "opening up," "stressing," breaking or shattering the biomass materials, making the cellulose of the materials more susceptible to chain scission and/or disruption of crystalline structure during the physical treatment.

Methods of mechanically treating the biomass material include, for example, milling or grinding. Milling may be performed using, for example, a mill, ball mill, colloid mill, conical or cone mill, disk mill, edge mill, Wiley mill, grist mill or other mill. Grinding may be performed using, for example, a cutting/impact type grinder. Some exemplary grinders include stone grinders, pin grinders, coffee grinders, and bun grinders. Grinding or milling may be provided, for example, by a reciprocating pin or other element, as is the case in a pin mill. Other mechanical treatment methods include mechanical ripping, tearing, shearing or chopping, other methods that apply pressure to the fibers, and air attrition milling. Suitable mechanical treatments further include any other technique that continues the disruption of the internal structure of the material that was initiated by the previous processing steps.

Mechanical feed preparation systems can be configured to produce streams with specific characteristics such as, for example, specific maximum sizes, specific length-to-width, or specific surface areas ratios. Physical preparation can increase the rate of reactions, improve the movement of material on a conveyor, improve the irradiation profile of the material, improve the radiation uniformity of the material, or reduce the processing time required by opening up the materials and making them more accessible to processes and/or reagents, such as reagents in a solution.

The bulk density of feedstocks can be controlled (e.g., increased). In some situations, it can be desirable to prepare a low bulk density material, e.g., by densifying the material (e.g., densification can make it easier and less costly to transport to another site) and then reverting the material to a lower bulk density state (e.g., after transport). The material can be densified, for example from less than about 0.2 g/cc to more than about 0.9 g/cc (e.g., less than about 0.3 to more than about 0.5 g/cc, less than about 0.3 to more than about 0.9 g/cc, less than about 0.5 to more than about 0.9 g/cc, less than about 0.3 to more than about 0.8 g/cc, less than about 0.2 to more than about 0.5 g/cc). For example, the material can be densified by the methods and equipment disclosed in U.S. Pat. No. 7,932,065 to Medoff and International Publication No. WO 2008/073186 (which was filed Oct. 26, 2007, was published in English, and which designated the United States), the full disclosures of which are incorporated herein by reference. Densified materials can be processed by any of the methods described herein, or any material processed by any of the methods described herein can be subsequently densified.

In some embodiments, the material to be processed is in the form of a fibrous material that includes fibers provided by shearing a fiber source. For example, the shearing can be performed with a rotary knife cutter.

For example, a fiber source, e.g., that is recalcitrant or that has had its recalcitrance level reduced, can be sheared, e.g., in a rotary knife cutter, to provide a first fibrous material. The first fibrous material is passed through a first screen, e.g., having an average opening size of 1.59 mm or less ($\frac{1}{16}$ inch, 0.0625 inch), provide a second fibrous material. If desired, the fiber source can be cut prior to the shearing, e.g., with a shredder. For example, when a paper is used as the fiber source, the paper can be first cut into strips that are, e.g., $\frac{1}{4}$- to $\frac{1}{2}$-inch wide, using a shredder, e.g., a counter-rotating screw shredder, such as those manufactured by Munson (Utica, N.Y.). As an alternative to shredding, the paper can be reduced in size by cutting to a desired size using a guillotine cutter. For example, the guillotine cutter can be used to cut the paper into sheets that are, e.g., 10 inches wide by 12 inches long.

In some embodiments, the shearing of the fiber source and the passing of the resulting first fibrous material through a first screen are performed concurrently. The shearing and the passing can also be performed in a batch-type process.

For example, a rotary knife cutter can be used to concurrently shear the fiber source and screen the first fibrous material. A rotary knife cutter includes a hopper that can be loaded with a shredded fiber source prepared by shredding a fiber source.

In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical treatments that may be used, and the characteristics of the mechanically treated biomass materials, are described in further detail in U.S. Pat. App. Pub. 2012/0100577 A1, filed Oct. 18, 2011, the full disclosure of which is hereby incorporated herein by reference.

Treatment of Biomass Material—Particle Bombardment

One or more treatments with energetic particle bombardment can be used to process raw feedstock from a wide variety of different sources to extract useful substances from the feedstock, and to provide partially degraded organic material which functions as input to further processing steps and/or sequences. Particle bombardment can reduce the molecular weight and/or crystallinity of feedstock. In some embodiments, energy deposited in a material that releases an electron from its atomic orbital can be used to treat the materials. The bombardment may be provided by heavy charged particles (such as alpha particles or protons), electrons (produced, for example, in beta decay or electron beam accelerators), or electromagnetic radiation (for example, gamma rays, x rays, or ultraviolet rays). Alternatively, radiation produced by radioactive substances can be used to treat the feedstock. Any combination, in any order, or concurrently of these treatments may be utilized. In another approach, electromagnetic radiation (e.g., produced using electron beam emitters) can be used to treat the feedstock.

Each form of energy ionizes the biomass via particular interactions. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part, due to their acidic nature. When particles are utilized, the particles can have the mass of a resting electron, or greater, e.g., 500, 1000, 1500, or 2000 or more times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 atomic units. Accelerators used to accelerate the particles can be electrostatic DC, electrodynamic DC, RF linear, magnetic induction linear or continuous wave. For example, cyclotron type accelerators are available from IBA (Ion Beam Accelerators, Louvain-la-Neuve, Belgium), such as the Rhodotron™ system, while DC type accelerators are available from RDI, now IBA Industrial, such as the Dynamitron™. Ions and ion accelerators are discussed in Introductory Nuclear Physics, Kenneth S. Krane, John Wiley & Sons, Inc. (1988), Krsto Prelec, FIZIKA B 6 (1997) 4, 177-206; Chu, William T., "Overview of Light-Ion Beam Therapy", Columbus-Ohio, ICRU-IAEA Meeting, 18-20 Mar. 2006; Iwata, Y. et al., "Alternating-Phase-Focused 1H-DTL for Heavy-Ion Medical Accelerators", Proceedings of EPAC 2006, Edinburgh, Scotland; and Leitner, C. M. et al., "Status of the Superconducting ECR Ion Source Venus", Proceedings of EPAC 2000, Vienna, Austria.

The doses applied depend on the desired effect and the particular feedstock. For example, high doses can break chemical bonds within feedstock components and low doses can increase chemical bonding (e.g., cross-linking) within feedstock components.

In some instances when chain scission is desirable and/or polymer chain functionalization is desirable, particles heavier than electrons, such as protons, helium nuclei, argon ions, silicon ions, neon ions, carbon ions, phosphorus ions, oxygen ions or nitrogen ions can be utilized. When ring-opening chain scission is desired, positively charged particles can be utilized for their Lewis acid properties for enhanced ring-opening chain scission. For example, when oxygen-containing functional groups are desired, treatment in the presence of oxygen or even treatment with oxygen ions can be performed. For example, when nitrogen-containing functional groups are desirable, treatment in the presence of nitrogen or even treatment with nitrogen ions can be performed.
Other Forms of Energy Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission.

Electromagnetic radiation interacts via three processes: photoelectric absorption, Compton scattering, and pair production. The dominating interaction is determined by the energy of the incident radiation and the atomic number of the material. The summation of interactions contributing to the absorbed radiation in cellulosic material can be expressed by the mass absorption coefficient.

Electromagnetic radiation is subclassified as gamma rays, x rays, ultraviolet rays, infrared rays, microwaves, or radiowaves, depending on the wavelength.

For example, gamma radiation can be employed to treat the materials. Gamma radiation has the advantage of a significant penetration depth into a variety of material in the sample. Sources of gamma rays include radioactive nuclei, such as isotopes of cobalt, calcium, technetium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

Various other devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No. 7,931,784 B2, the complete disclosure of which is incorporated herein by reference.
Treatment of Biomass Material—Electron Bombardment The feedstock may be treated with electron bombardment to modify its structure and thereby reduce its recalcitrance. Such treatment may, for example, reduce the average molecular weight of the feedstock, change the crystalline structure of the feedstock, and/or increase the surface area and/or porosity of the feedstock.

Electron bombardment via an electron beam is generally preferred, because it provides very high throughput and because the use of a relatively low voltage/high power electron beam device eliminates the need for expensive concrete vault shielding, as such devices are "self-shielded" and provide a safe, efficient process. While the "self-shielded" devices do include shielding (e.g., metal plate shielding), they do not require the construction of a concrete vault, greatly reducing capital expenditure and often allowing an existing manufacturing facility to be used without expensive modification. Electron beam accelerators are available, for example, from IBA (Ion Beam Applications, Louvain-la-Neuve, Belgium), Titan Corporation (San Diego, Calif., USA), and NHV Corporation (Nippon High Voltage, Japan).

Electron bombardment may be performed using an electron beam device that has a nominal energy of less than 10 MeV, e.g., less than 7 MeV, less than 5 MeV, or less than 2 MeV, e.g., from about 0.5 to 1.5 MeV, from about 0.8 to 1.8 MeV, from about 0.7 to 1 MeV, or from about 1 to 3 MeV. In some implementations the nominal energy is about 500 to 800 keV.

The electron beam may have a relatively high total beam power (the combined beam power of all accelerating heads, or, if multiple accelerators are used, of all accelerators and all heads), e.g., at least 25 kW, e.g., at least 30, 40, 50, 60, 65, 70, 80, 100, 125, or 150 kW. In some cases, the power is even as high as 500 kW, 750 kW, or even 1000 kW or more. In some cases the electron beam has a beam power of 1200 kW or more.

This high total beam power is usually achieved by utilizing multiple accelerating heads. For example, the electron beam device may include two, four, or more accelerating heads. The use of multiple heads, each of which has a relatively low beam power, prevents excessive temperature rise in the material, thereby preventing burning of the material, and also increases the uniformity of the dose through the thickness of the layer of material.

In some implementations, it is desirable to cool the material during electron bombardment. For example, the material can be cooled while it is being conveyed, for example by a screw extruder or other conveying equipment.

To reduce the energy required by the recalcitrance-reducing process, it is desirable to treat the material as quickly as possible. In general, it is preferred that treatment be performed at a dose rate of greater than about 0.25 Mrad per second, e.g., greater than about 0.5, 0.75, 1, 1.5, 2, 5, 7, 10, 12, 15, or even greater than about 20 Mrad per second, e.g., about 0.25 to 2 Mrad per second. Higher dose rates generally require higher line speeds, to avoid thermal decomposition of the material. In one implementation, the accelerator is set for 3 MeV, 50 mAmp beam current, and the line speed is 24 feet/minute, for a sample thickness of about 20 mm (e.g., comminuted corn cob material with a bulk density of 0.5 g/cm$^3$).

In some embodiments, electron bombardment is performed until the material receives a total dose of at least 0.5 Mrad, e.g., at least 5, 10, 20, 30 or at least 40 Mrad. In some embodiments, the treatment is performed until the material receives a dose of from about 0.5 Mrad to about 150 Mrad, about 1 Mrad to about 100 Mrad, about 2 Mrad to about 75 Mrad, 10 Mrad to about 50 Mrad, e.g., about 5 Mrad to about 50 Mrad, from about 20 Mrad to about 40 Mrad, about 10 Mrad to about 35 Mrad, or from about 25 Mrad to about 30 Mrad. In some implementations, a total dose of 25 to 35 Mrad is preferred, applied ideally over a couple of seconds, e.g., at 5 Mrad/pass with each pass being applied for about one second. Applying a dose of greater than 7 to 8 Mrad/pass can in some cases cause thermal degradation of the feedstock material.

Using multiple heads as discussed above, the material can be treated in multiple passes, for example, two passes at 10 to 20 Mrad/pass, e.g., 12 to 18 Mrad/pass, separated by a few seconds of cool-down, or three passes of 7 to 12 Mrad/pass, e.g., 9 to 11 Mrad/pass. As discussed above, treating the material with several relatively low doses, rather than one high dose, tends to prevent overheating of the material and also increases dose uniformity through the thickness of the material. In some implementations, the material is stirred or otherwise mixed during or after each pass and then smoothed into a uniform layer again before the next pass, to further enhance treatment uniformity.

In some embodiments, electrons are accelerated to, for example, a speed of greater than 75 percent of the speed of light, e.g., greater than 85, 90, 95, or 99 percent of the speed of light.

In some embodiments, any processing described herein occurs on lignocellulosic material that remains dry as acquired or that has been dried, e.g., using heat and/or reduced pressure. For example, in some embodiments, the cellulosic and/or lignocellulosic material has less than about five percent by weight retained water, measured at 25° C. and at fifty percent relative humidity.

Electron bombardment can be applied while the cellulosic and/or lignocellulosic material is exposed to air, oxygen-enriched air, or even oxygen itself, or blanketed by an inert gas such as nitrogen, argon, or helium. When maximum oxidation is desired, an oxidizing environment is utilized, such as air or oxygen and the distance from the beam source is optimized to maximize reactive gas formation, e.g., ozone and/or oxides of nitrogen.

In some embodiments, two or more electron sources are used, such as two or more ionizing sources. For example, samples can be treated, in any order, with a beam of electrons, followed by gamma radiation and UV light having wavelengths from about 100 nm to about 280 nm. In some embodiments, samples are treated with three ionizing radiation sources, such as a beam of electrons, gamma radiation, and energetic UV light. The biomass is conveyed through the treatment zone where it can be bombarded with electrons. It is generally preferred that the bed of biomass material has a relatively uniform thickness, as previously described, while being treated.

It may be advantageous to repeat the treatment to more thoroughly reduce the recalcitrance of the biomass and/or further modify the biomass. In particular the process parameters can be adjusted after a first (e.g., second, third, fourth or more) pass depending on the recalcitrance of the material. In some embodiments, a conveyor can be used which includes a circular system where the biomass is conveyed multiple times through the various processes described above. In some other embodiments multiple treatment devices (e.g., electron beam generators) are used to treat the biomass multiple (e.g., 2, 3, 4 or more) times. In yet other embodiments, a single electron beam generator may be the source of multiple beams (e.g., 2, 3, 4 or more beams) that can be used for treatment of the biomass.

The effectiveness in changing the molecular/supermolecular structure and/or reducing the recalcitrance of the biomass depends on the electron energy used and the dose applied, while exposure time depends on the power and dose.

In some embodiments, the treatment (with any electron source or a combination of sources) is performed until the material receives a dose of at least about 0.05 Mrad, e.g., at least about 0.1, 0.25, 0.5, 0.75, 1.0, 2.5, 5.0, 7.5, 10.0, 15, 20, 25, 30, 40, 50, 60, 70, 80, 90, 100, 125, 150, 175, or 200 Mrad. In some embodiments, the treatment is performed until the material receives a dose of between 0.1-100 Mrad, 1-200, 5-200, 10-200, 5-150, 5-100, 5-50, 5-40, 10-50, 10-75, 15-50, 20-35 Mrad.

In some embodiments, the treatment is performed at a dose rate of between 5.0 and 1500.0 kilorads/hour, e.g., between 10.0 and 750.0 kilorads/hour or between 50.0 and 350.0 kilorads/hours. In other embodiments, the treatment is performed at a dose rate of between 10 and 10000 kilorads/hr, between 100 and 1000 kilorad/hr, or between 500 and 1000 kilorads/hr.

Electron Sources

Electrons interact via Coulomb scattering and bremsstrahlung radiation produced by changes in the velocity of electrons. Electrons may be produced by radioactive nuclei that undergo beta decay, such as isotopes of iodine, cesium, technetium, and iridium. Alternatively, an electron gun can be used as an electron source via thermionic emission and accelerated through an accelerating potential. An electron gun generates electrons, accelerates them through a large potential (e.g., greater than about 500 thousand, greater than about 1 million, greater than about 2 million, greater than about 5 million, greater than about 6 million, greater than about 7 million, greater than about 8 million, greater than about 9 million, or even greater than 10 million volts) and then scans them magnetically in the x-y plane, where the electrons are initially accelerated in the z direction down the tube and extracted through a foil window. Scanning the electron beam is useful for increasing the irradiation surface when irradiating materials, e.g., a biomass, that is conveyed through the scanned beam. Scanning the electron beam also distributes the thermal load homogenously on the window and helps reduce the foil window rupture due to local heating by the electron beam. Window foil rupture is a cause of significant down-time due to subsequent necessary repairs and re-starting the electron gun.

Various other irradiating devices may be used in the methods disclosed herein, including field ionization sources, electrostatic ion separators, field ionization generators, thermionic emission sources, microwave discharge ion sources, recirculating or static accelerators, dynamic linear accelerators, van de Graaff accelerators, and folded tandem accelerators. Such devices are disclosed, for example, in U.S. Pat. No.

7,931,784 to Medoff, the complete disclosure of which is incorporated herein by reference.

A beam of electrons can be used as the radiation source. A beam of electrons has the advantages of high dose rates (e.g., 1, 5, or even 10 Mrad per second), high throughput, less containment, and less confinement equipment. Electron beams can also have high electrical efficiency (e.g., 80%), allowing for lower energy usage relative to other radiation methods, which can translate into a lower cost of operation and lower greenhouse gas emissions corresponding to the smaller amount of energy used. Electron beams can be generated, e.g., by electrostatic generators, cascade generators, transformer generators, low energy accelerators with a scanning system, low energy accelerators with a linear cathode, linear accelerators, and pulsed accelerators.

Electrons can also be more efficient at causing changes in the molecular structure of biomass materials, for example, by the mechanism of chain scission. In addition, electrons having energies of 0.5-10 MeV can penetrate low density materials, such as the biomass materials described herein, e.g., materials having a bulk density of less than 0.5 g/cm$^3$, and a depth of 0.3-10 cm. Electrons as an ionizing radiation source can be useful, e.g., for relatively thin piles, layers or beds of materials, e.g., less than about 0.5 inch, e.g., less than about 0.4 inch, 0.3 inch, 0.25 inch, or less than about 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV. Methods of irradiating materials are discussed in U.S. Pat. App. Pub. 2012/0100577 A1, filed Oct. 18, 2011, the entire disclosure of which is herein incorporated by reference.

Electron beam irradiation devices may be procured commercially from Ion Beam Applications (Louvain-la-Neuve, Belgium), the Titan Corporation (San Diego, Calif., USA), and NHV Corporation (Nippon High Voltage, Japan). Typical electron energies can be 0.5 MeV, 1 MeV, 2 MeV, 4.5 MeV, 7.5 MeV, or 10 MeV. Typical electron beam irradiation device power can be 1 KW, 5 KW, 10 KW, 20 KW, 50 KW, 60 KW, 70 KW, 80 KW, 90 KW, 100 KW, 125 KW, 150 KW, 175 KW, 200 KW, 250 KW, 300 KW, 350 KW, 400 KW, 450 KW, 500 KW, 600 KW, 700 KW, 800 KW, 900 KW or even 1000 KW.

Tradeoffs in considering electron beam irradiation device power specifications include cost to operate, capital costs, depreciation, and device footprint. Tradeoffs in considering exposure dose levels of electron beam irradiation would be energy costs and environment, safety, and health (ESH) concerns. Typically, generators are housed in a vault, e.g., of lead or concrete, especially for production from X-rays that are generated in the process. Tradeoffs in considering electron energies include energy costs.

The electron beam irradiation device can produce either a fixed beam or a scanning beam. A scanning beam may be advantageous with large scan sweep length and high scan speeds, as this would effectively replace a large, fixed beam width. Further, available sweep widths of 0.5 m, 1 m, 2 m or more are available. The scanning beam is preferred in most embodiments describe herein because of the larger scan width and reduced possibility of local heating and failure of the windows.

Treatment of Biomass Material—Sonication, Pyrolysis, Oxidation, Steam Explosion

If desired, one or more sonication, pyrolysis, oxidative, or steam explosion processes can be used in addition to or instead of other treatments to further reduce the recalcitrance of the biomass material. These processes can be applied before, during and/or after another treatment or treatments. These processes are described in detail in U.S. Pat. No. 7,932,065 to Medoff, the full disclosure of which is incorporated herein by reference.

Use of Treated Biomass Material

Using the methods described herein, a starting biomass material (e.g., plant biomass, animal biomass, paper, and municipal waste biomass) can be used as feedstock to produce useful intermediates and products such as organic acids, salts of organic acids, anhydrides, esters of organic acids and fuels, e.g., fuels for internal combustion engines or feedstocks for fuel cells. Systems and processes are described herein that can use as feedstock cellulosic and/or lignocellulosic materials that are readily available, but often can be difficult to process, e.g., municipal waste streams and waste paper streams, such as streams that include newspaper, kraft paper, corrugated paper or mixtures of these.

In order to convert the feedstock to a form that can be readily processed, the glucan- or xylan-containing cellulose in the feedstock can be hydrolyzed to low molecular weight carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The feedstock can be hydrolyzed using an enzyme, e.g., by combining the materials and the enzyme in a solvent, e.g., in an aqueous solution.

Alternatively, the enzymes can be supplied by organisms that break down biomass, such as the cellulose and/or the lignin portions of the biomass, contain or manufacture various cellulolytic enzymes (cellulases), ligninases or various small molecule biomass-degrading metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (beta-glucosidases).

During saccharification a cellulosic substrate can be initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally, cellobiase cleaves cellobiose to yield glucose. The efficiency (e.g., time to hydrolyze and/or completeness of hydrolysis) of this process depends on the recalcitrance of the cellulosic material.

Intermediates and Products

The processes described herein are preferably used to produce butanol, e.g., isobutanol or n-butanol, and derivatives. However, the processes may be used to produce other products, co-products and intermediates, for example, the products described in U.S. Pat. App. Pub. 2012/0100577 A1, filed Oct. 18, 2011 and published Apr. 26, 2012, the full disclosure of which is incorporated herein by reference.

Using the processes described herein, the biomass material can be converted to one or more products, such as energy, fuels, foods and materials. Specific examples of products include, but are not limited to, hydrogen, sugars (e.g., glucose, xylose, arabinose, mannose, galactose, fructose, disaccharides, oligosaccharides and polysaccharides), alcohols (e.g., monohydric alcohols or dihydric alcohols, such as ethanol, n-propanol, isobutanol, sec-butanol, tert-butanol or n-butanol), hydrated or hydrous alcohols (e.g., containing greater than 10%, 20%, 30% or even greater than 40% water), biodiesel, organic acids, hydrocarbons (e.g., methane, ethane, propane, isobutene, pentane, n-hexane, biodiesel, bio-gasoline and mixtures thereof), co-products (e.g., proteins, such as cellulolytic proteins (enzymes) or single cell proteins), and mixtures of any of these in any combination or relative concentration, and optionally in combination with any additives (e.g., fuel additives). Other examples include carboxylic acids, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha and beta unsaturated acids (e.g., acrylic acid) and olefins (e.g., ethylene). Other alcohols and alcohol derivatives include propanol, propylene glycol, 1,4-butanediol, 1,3-propanediol, sugar alcohols and polyols (e.g., glycol, glycerol, erythritol, threitol, arabitol, xylitol, ribitol, mannitol, sorbitol, galactitol, iditol, inositol, volemitol, isomalt, maltitol, lactitol, maltotriitol, maltotetraitol, and polyglycitol and other polyols), and methyl or ethyl esters of any of these alcohols. Other products include methyl acrylate, methylmethacrylate, lactic acid, citric acid, formic acid, acetic acid, propionic acid, butyric acid, succinic acid, valeric acid, caproic acid, 3-hydroxypropionic acid, palmitic acid, stearic acid, oxalic acid, malonic acid, glutaric acid, oleic acid, linoleic acid, glycolic acid, gamma-hydroxybutyric acid, and mixtures thereof, salts of any of these acids, mixtures of any of the acids and their respective salts.

Any combination of the above products with each other, and/or of the above products with other products, which other products may be made by the processes described herein or otherwise, may be packaged together and sold as products. The products may be combined, e.g., mixed, blended or co-dissolved, or may simply be packaged or sold together.

Any of the products or combinations of products described herein may be sanitized or sterilized prior to selling the products, e.g., after purification or isolation or even after packaging, to neutralize one or more potentially undesirable contaminants that could be present in the product(s). Such sanitation can be done with electron bombardment, for example, be at a dosage of less than about 20 Mrad, e.g., from about 0.1 to 15 Mrad, from about 0.5 to 7 Mrad, or from about 1 to 3 Mrad.

The processes described herein can produce various by-product streams useful for generating steam and electricity to be used in other parts of the plant (co-generation) or sold on the open market. For example, steam generated from burning by-product streams can be used in a distillation process. As another example, electricity generated from burning by-product streams can be used to power electron beam generators used in pretreatment.

The by-products used to generate steam and electricity are derived from a number of sources throughout the process. For example, anaerobic digestion of wastewater can produce a biogas high in methane and a small amount of waste biomass (sludge). As another example, post-saccharification and/or post-distillate solids (e.g., unconverted lignin, cellulose, and hemicellulose remaining from the pretreatment and primary processes) can be used, e.g., burned, as a fuel.

Many of the products obtained, such as ethanol or n-butanol, can be utilized as a fuel for powering cars, trucks, tractors, ships or trains, e.g., as an internal combustion fuel or as a fuel cell feedstock. Many of the products obtained can also be utilized to power aircraft, such as planes, e.g., having jet engines or helicopters. In addition, the products described herein can be utilized for electrical power generation, e.g., in a conventional steam generating plant or in a fuel cell plant.

Other intermediates and products, including food and pharmaceutical products, are described in U.S. Pat. App. Pub. 2010/0124583 A1, published May 20, 2010, to Medoff, the full disclosure of which is hereby incorporated by reference herein.

Saccharification

To obtain a fructose solution from the reduced-relacitrance feedstock, the treated biomass materials can be saccharified and then isomerized and optionally purified, generally by combining the material and a cellulase enzyme in a fluid medium, e.g., an aqueous solution. In some cases, the material is boiled, steeped, or cooked in hot water prior to saccharification, as described in U.S. Pat. App. Pub. 2012/0100577 A1 by Medoff and Masterman, published on Apr. 26, 2012, the entire contents of which are incorporated herein.

The saccharification process can be partially or completely performed in a tank (e.g., a tank having a volume of at least 4000, 40,000, or 500,000 L) in a manufacturing plant, and/or can be partially or completely performed in transit, e.g., in a rail car, tanker truck, or in a supertanker or the hold of a ship. The time required for complete saccharification will depend on the process conditions and the biomass material and enzyme used. If saccharification is performed in a manufacturing plant under controlled conditions, the cellulose may be substantially entirely converted to sugar, e.g., glucose in about 12-96 hours. If saccharification is performed partially or completely in transit, saccharification may take longer.

It is generally preferred that the tank contents be mixed during saccharification, e.g., using jet mixing as described in International App. No. PCT/US2010/035331, filed May 18, 2010, which was published in English as WO 2010/135380 and designated the United States, the full disclosure of which is incorporated by reference herein.

The addition of surfactants can enhance the rate of saccharification. Examples of surfactants include non-ionic surfactants, such as a TWEEN® 20 or TWEEN® 80 polyethylene glycol surfactants, ionic surfactants, or amphoteric surfactants.

It is generally preferred that the concentration of the sugar solution resulting from saccharification be relatively high, e.g., greater than 40%, or greater than 50, 60, 70, 80, 90 or even greater than 95% by weight. Water may be removed, e.g., by evaporation, to increase the concentration of the sugar solution. This reduces the volume to be shipped, and also inhibits microbial growth in the solution.

The concentration of fructose solutions, for example, after isomerization of a saccharified solution, can be between about 1 an 40%. For example, between about 5 and 40%, between about 10 and 40%, between about 15 and 40%, between about 5 and 10%, between about 10% and 30% and between about 30% and 40%.

Other sources of fructose can also be utilized. For example fructose can be obtained from Molasses. Some examples of different kinds of molasses are Sugar Cane Molasses, Citrus Molasses, Starch Molasses, Blackstrap Molasses and/or Sugar Beet Molasses. Glucose in molasses can range between about 30% to 70% (e.g., 40% to 60%, eg., 45% to 55%) of the glucose/fructose total, for example high fructose corn syrup is 55% fructose and 45% glucose. Extracts from fruits can also be a source of high fructose products, for example, agava extract can have 90% fructose and 10% glucose. The isomerization of glucose solutions can increase the concentrations of glucose solutions and is another source of fructose. Isomerization can be done by an isomerase as discussed herein. Another source of fructose is the hydrolysis of sucrose, for example using an enzyme (e.g., sucarase), using and acid and/or using a base.

Alternatively, sugar solutions of lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high. Alternatively, other additives with anti-microbial of preservative properties may be used. Preferably the antimicrobial additive(s) are food-grade.

A relatively high concentration solution can be obtained by limiting the amount of water added to the biomass material with the enzyme. The concentration can be controlled, e.g., by controlling how much saccharification takes place. For example, concentration can be increased by adding more biomass material to the solution. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

By adding glucose isomerase to the contents of the tank, a high concentration of fructose can be obtained without saccharification being inhibited by the sugars in the tank. Glucose isomerase can be added in any amount. For example, the concentration may be below about 500 U/g of cellulose (lower than or equal to 100 U/g cellulose, lower than or equal to 50 U/g cellulose, lower than or equal to 10 U/g cellulose, lower than or equal to 5 U/g cellulose). The concentration is at least about 0.1 U/g cellulose (at least about 0.5 U/g cellulose, at least about 1 U/g cellulose, at least about 2 U/g cellulose, at least about 3 U/g cellulose).

The addition of glucose isomerase increases the amount of sugars produced by at least 5% (at least 10%, at least to 15%, at least 20%).

The concentration of sugars in the solution can also be enhanced by limiting the amount of water added to the feedstock with the enzyme, and/or the concentration can be increased by adding more feedstock to the solution during saccharification. In order to keep the sugar that is being produced in solution, a surfactant can be added, e.g., one of those discussed above. Solubility can also be increased by increasing the temperature of the solution. For example, the solution can be maintained at a temperature of 40-50° C., 60-80° C., or even higher.

Saccharifying Agents

Suitable cellulolytic enzymes include cellulases from species in the genera *Bacillus, Coprinus, Myceliophthora, Cephalosporium, Scytalidium, Penicillium, Aspergillus, Pseudomonas, Humicola, Fusarium, Thielavia, Acremonium, Chrysosporium* and *Trichoderma*, especially those produced by a strain selected from the species *Aspergillus* (see, e.g., EP Pub. No. 0 458 162), *Humicola insolens* (reclassified as *Scytalidium thermophilum*, see, e.g., U.S. Pat. No. 4,435, 307), *Coprinus cinereus, Fusarium oxysporum, Myceliophthora thermophila, Meripilus giganteus, Thielavia terrestris, Acremonium* sp. (including, but not limited to, *A. persicinum, A. acremonium, A. brachypenium, A. dichromosporum, A. obclavatum, A. pinkertoniae, A. roseogriseum, A. incoloratum,* and *A. furatum*). Preferred strains include *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from Chrysosporium, preferably a strain of Chrysosporium lucknowense. Additional strains that can be used include, but are not limited to, *Trichoderma* (particularly *T. viride, T. reesei,* and *T. koningii*), alkalophilic *Bacillus* (see, for example, U.S. Pat. No. 3,844,890 and EP Pub. No. 0 458 162), and *Streptomyces* (see, e.g., EP Pub. No. 0 458 162).

Many microorganisms that can be used to saccharify biomass material and produce sugars can also be used to ferment and convert those sugars to useful products.

Sugars

In the processes described herein, for example after saccharification, sugars (e.g., glucose and xylose) can be isolated. For example, sugars can be isolated by precipitation, crystallization, chromatography (e.g., simulated moving bed chromatography, high pressure chromatography), centrifugation, extraction, any other isolation method known in the art, and combinations thereof.

Hydrogenation and Other Chemical Transformations

The processes described herein can include hydrogenation. For example glucose and xylose can be hydrogenated to sorbitol and xylitol respectively. Hydrogenation can be accomplished by use of a catalyst (e.g., Pt/gamma-$Al_2O_3$, Ru/C, Raney Nickel, or other catalysts known in the art) in combination with $H_2$ under high pressure (e.g., 10 to 12000 psi). Other types of chemical transformation of the products from the processes described herein can be used, for example, production of organic sugar derived products such as furfural and furfural-derived products. Chemical transformations of sugar derived products are described in U.S. application Ser. No. 13/934,704, filed Jul. 3, 2013, the disclosure of which is incorporated herein by reference in its entirety.

Fermentation

Preferably, *Clostridium* spp. are used to convert sugars (e.g., fructose) to butanol. The optimum pH for fermentations is about pH 4 to 7. For example, the optimum pH for yeast is from about pH 4 to 5, while the optimum pH for *Zymomonas* is from about pH 5 to 6. Typical fermentation times are about 24 to 168 hours (e.g., 24 to 96 hrs) with temperatures in the range of 20° C. to 40° C. (e.g., 26° C. to 40° C.), however thermophilic microorganisms prefer higher temperatures.

In some embodiments, e.g., when anaerobic organisms are used, at least a portion of the fermentation is conducted in the absence of oxygen, e.g., under a blanket of an inert gas such as $N_2$, Ar, He, $CO_2$ or mixtures thereof. Additionally, the mixture may have a constant purge of an inert gas flowing through the tank during part of or all of the fermentation. In some cases, anaerobic condition, can be achieved or maintained by carbon dioxide production during the fermentation and no additional inert gas is needed.

In some embodiments, all or a portion of the fermentation process can be interrupted before the low molecular weight sugar is completely converted to a product (e.g., ethanol). The intermediate fermentation products include sugar and carbohydrates in high concentrations. The sugars and carbohydrates can be isolated via any means known in the art. These intermediate fermentation products can be used in preparation of food for human or animal consumption. Additionally or alternatively, the intermediate fermentation products can be ground to a fine particle size in a stainless-steel laboratory mill to produce a flour-like substance.

Jet mixing may be used during fermentation, and in some cases saccharification and fermentation are performed in the same tank.

Nutrients for the microorganisms may be added during saccharification and/or fermentation, for example the food-based nutrient packages described in U.S. Pat. App. Pub. 2012/0052536, filed Jul. 15, 2011, the complete disclosure of which is incorporated herein by reference.

"Fermentation" includes the methods and products that are disclosed in International App. No. PCT/US2012/71083, the content of which are incorporated by reference herein in their entirety.

Mobile fermenters can be utilized, as described in International App. No. PCT/US2007/074028 (which was filed Jul. 20, 2007, was published in English as WO 2008/011598 and designated the United States), the contents of which is incorporated herein in its entirety. Similarly, the saccharification equipment can be mobile. Further, saccharification and/or fermentation may be performed in part or entirely during transit.

Other Fermentation Agents

Although *Clostridium* is preferred, other microorganisms can be used. For instance, yeast and *Zymomonas* bacteria can be used for fermentation or conversion of sugar(s) to other alcohol(s). Other microorganisms are discussed below. They can be naturally-occurring microorganisms and/or engineered microorganisms. For example, the microorganism can be a bacterium (including, but not limited to, e.g., a cellulolytic bacterium), a fungus, (including, but not limited to, e.g., a yeast), a plant, a protist, e.g., a protozoa or a fungus-like protest (including, but not limited to, e.g., a slime mold), or an alga. When the organisms are compatible, mixtures of organisms can be utilized.

Suitable fermenting microorganisms have the ability to convert carbohydrates, such as glucose, fructose, xylose, arabinose, mannose, galactose, oligosaccharides or polysaccharides into fermentation products. Fermenting microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii* (Philippidis, G. P., 1996, Cellulose bioconversion technology, in Handbook on Bioethanol: Production and Utilization, Wyman, C. E., ed., Taylor & Francis, Washington, D.C., 179-212)). Other suitable microorganisms include, for example, *Zymomonas mobilis, Clostridium* spp. (including, but not limited to, *C. thermocellum* (Philippidis, 1996, supra), *C. saccharobutylacetonicum, C. saccharobutylicum, C. Puniceum, C. beijernckii*, and *C. acetobutylicum*), *Moniliella pollinis, Moniliella megachiliensis, Lactobacillus* spp. *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnoliae, Ustilaginomycetes* sp., *Pseudozyma tsukubaensis*, yeast species of genera *Zygosaccharomyces, Debaryomyces, Hansenula* and *Pichia*, and fungi of the dematioid genus *Torula*.

For instance, *Clostridium* spp. can be used to produce ethanol, butanol, butyric acid, acetic acid, and acetone. *Lactobacillus* spp., can be used to produce lactic acid.

Many such microbial strains are publicly available, either commercially or through depositories such as the ATCC (American Type Culture Collection, Manassas, Va., USA), the NRRL (Agricultural Research Service Culture Collection, Peoria, Ill., USA), or the DSMZ (Deutsche Sammlung von Mikroorganismen and Zellkulturen GmbH, Braunschweig, Germany), to name a few.

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Many microorganisms that can be used to saccharify biomass material and produce sugars can also be used to ferment and convert those sugars to useful products.

Distillation

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

EXAMPLES

Example 1

Butanol Production on Glucose, Xylose and Fructose

A P2 based medium as described in U.S. Pat. No. 6,358, 717 was used for the following tests. The medium was composed of the following separately prepared solutions (in grams per 100 ml of distilled water, unless indicated otherwise): sugar (see below for types and amounts), 790 ml of distilled water (solution I), 0.5 g of $K_2HPO_4$, 0.5 g of $KH_2PO_4$, 2.2 g of $CH_3COONH_4$ (solution II), 2.0 g of $MgSO_4.7H_2O$, 0.1 g of $MnSO_4.H_2O$, 0.1 g of NaCl, 0.1 g of $FeSO_4.7H_2O$ (solution III), and 100 mg of p-aminobenzoic acid, 100 mg of thiamine, 1 mg of biotin (solution IV). Solutions I and II were filter sterilized and subsequently mixed to form a sugar buffer solution. Solutions III and IV were filter sterilized. Portions (10 and 1 ml) of solutions III and IV, respectively, were added aseptically to the sugar-buffer solution. The final pH of the P2 medium was 6.6.

The amounts of sugars used were: for medium GXP2, 43 g glucose and 24 g xylose; for medium FP2, 43 g of fructose; for medium FGP2, 43 g fructose and 43 g glucose.

The solutions were sparged with argon for 45 min and then brought into an anaerobic chamber. Solutions (10 mL) were measured into 21, 20 mL previously autoclaved serum vials. The vials were sealed with a sealable septum and then brought out of the anaerobic box. Vials were inoculated with 1 vol % Clostridium saccharoperbutylacetonicum (ATCC 27021) from an aqueous glycerol stock prepared following the ATCC recommended protocol from the ATCC provided pellet. The vials were grown at 30° C. for 48 or 96 hours. The head space was analyzed for butanol production using GC. The results (in g/L) are shown in the table below.

TABLE 2

Results of butanol production on three different carbon sources.

| Sample ID | Time Point | Media | n-Butanol |
|---|---|---|---|
| 1 | 48 hr | GXP2 | 3.2 |
| 2 | 48 hr | GXP2 | 2.9 |
| 3 | 48 hr | GXP2 | 2.0 |
| 4 | 48 hr | FP2 | 11.5 |
| 5 | 48 hr | FP2 | 11.0 |
| 6 | 48 hr | FP2 | 11.7 |
| 7 | 48 hr | FGP2 | 3.1 |
| 8 | 48 hr | FGP2 | 3.0 |
| 9 | 48 hr | FGP2 | 3.5 |
| 10 | 96 hr | GXP2 | 2.6 |
| 11 | 96 hr | GXP2 | 2.9 |
| 12 | 96 hr | GXP2 | 3.0 |
| Control-13 | 96 hr | GXP2 | 0.0 |
| 14 | 96 hr | FP2 | 11.1 |
| 15 | 96 hr | FP2 | 12.0 |
| 16 | 96 hr | FP2 | 11.4 |
| Control-17 | 96 hr | FP2 | 0.0 |
| 18 | 96 hr | FGP2 | 2.3 |
| 19 | 96 hr | FGP2 | 2.7 |
| 20 | 96 hr | FGP2 | 3.4 |
| Control-21 | 96 hr | FGP2 | 0.0 |

Example 2

Butanol Production on Fructose Vs. Glucose & Xylose

Ten ml of P2 media containing either a glucose/xylose mixture of fructose alone (32 g/L) were incubated at 30° C. with one of either Clostridium saccharoperbutylacetonium ATCC strain 27021 or 27022. As in Example 1, the results presented in the table below show that more butanol is generated when Clostridium is grown on fructose, as opposed to glucose or xylose.

TABLE 3

Clostridium vial growth on fructose or glucose/xylose as the carbon source.

| Strain | Substrate | Butanol Production (g/L) | Timepoint (hrs) |
|---|---|---|---|
| ATCC 27021 | Fructose | 11.7 | 48 |
| ATCC 27021 | Glucose/Xylose | 2.3 | 48 |
| ATCC 27022 | Fructose | 11.6 | 96 |
| ATCC 27022 | Glucose/Xylose | 4.0 | 96 |

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for producing a product, the method comprising:
producing fructose by saccharifying a biomass and contacting the saccharified biomass with an isomerization agent selected to convert glucose to fructose, and converting the fructose to a product with a microorganism while maintaining metabolic conditions that cause the microorganism to produce a protective substrate effective to protect the microorganism from a toxic effect of the product.

2. The method of claim 1, wherein the biomass comprises a cellulosic or lignocellulosic material.

3. The method of claim 2, wherein the cellulosic or lignocellulosic biomass is treated to reduce its recalcitrance to saccharification.

4. The method of claim 3, wherein the treatment method is selected from the group consisting of: bombardment with electrons, sonication, oxidation, pyrolysis, steam explosion, chemical treatment, mechanical treatment, freeze grinding and combination thereof.

5. The method of claim 4, wherein the treatment method is bombardment with electrons.

6. The method of claim 2, wherein the cellulosic or lignocellulosic biomass is selected from the group consisting of: paper, paper products, paper waste, paper pulp, pigmented papers, loaded papers, coated papers, filled papers, magazines, printed matter, printer paper, polycoated paper, card stock, cardboard, paperboard, cotton, wood, particle board, forestry wastes, sawdust, aspen wood, wood chips, grasses, switchgrass, miscanthus, cord grass, reed canary grass, grain residues, rice hulls, oat hulls, wheat chaff, barley hulls, agricultural waste, silage, canola straw, wheat straw, barley straw, oat straw, rice straw, jute, hemp, flax, bamboo, sisal, abaca, corn cobs, corn stover, soybean stover, corn fiber, alfalfa, hay, coconut hair, sugar processing residues, bagasse, beet pulp, agave bagasse, algae, seaweed, manure, sewage, arracacha, buckwheat, banana, barley, cassava, kudzu, oca, sago, sorghum, potato, sweet potato, taro, yams, beans, favas, lentils, peas, industrial waste, and mixtures of any of these.

7. The method of claim 1, wherein the isomerization agent is an isomerase.

8. The method of claim 7, wherein the isomerase is xylose isomerase.

9. The method of claim 1, wherein the microorganism comprises a strain of *Clostridium* spp.

10. The method of claim 9, wherein the microorganism is *Clostridium saccharoperbutylacetonicum*.

11. The method of claim 10, wherein the microorganism is *Clostridium saccharoperbutylacetonicum* strain, ATCC 27021.

12. The method of claim 10, wherein the microorganism is *Clostridium saccharoperbutylacetonicum* strain, ATCC 27022.

13. The method of claim 9, wherein the alcohol comprises isobutanol or n-butanol.

14. The method of claim 1, wherein the product comprises a solvent.

15. The method of claim 14, wherein the solvent comprises an alcohol.

16. The method of claim 1, wherein the protective substrate comprises a triglyceride.

17. The method of claim 16, wherein the triglyceride is produced by esterification of glycerol 3-phosphate through a D-glyceraldehyde pathway.

* * * * *